United States Patent [19]

Privat

[11] Patent Number: 4,966,550
[45] Date of Patent: Oct. 30, 1990

[54] FILTER DEVICE

[76] Inventor: Richard F. Privat, 23920 Walling Rd., Geyersville, Calif. 95441

[21] Appl. No.: 396,551

[22] Filed: Aug. 21, 1989

Related U.S. Application Data

[63] Continuation-in-part of Ser. No. 7,185,896, Apr. 25, 1988, abandoned.

[51] Int. Cl.⁵ .............................................. A61C 3/00
[52] U.S. Cl. ...................................... 433/25; 55/274; 210/446
[58] Field of Search ................ 433/80, 82, 25; 55/274; 210/446

[56] References Cited

U.S. PATENT DOCUMENTS

| | | | |
|---|---|---|---|
| 3,360,128 | 12/1987 | Federline | 210/446 X |
| 3,696,932 | 10/1972 | Rosenberg | 210/446 X |
| 4,083,706 | 4/1978 | Wiley | 55/503 X |
| 4,601,820 | 7/1986 | Leason | 210/446 X |
| 4,741,697 | 5/1988 | Herbison | 55/27 X |
| 4,759,842 | 7/1988 | Frees et al. | 210/446 X |

Primary Examiner—John J. Wilson
Assistant Examiner—Nicholas D. Lucchesi
Attorney, Agent, or Firm—Larry D. Johnson

[57] ABSTRACT

A filter device comprises a clear plastic cylinder member with a pair of ends each bearing fittings conditioned to connect to an existing air supply line. At least one of the fittings bears a quick-release feature enabling ready access to that end of the cylinder member. The cylinder provides a housing for one or more standard cotton rolls, such as those typically used in a dental office, which provide the filtering medium. Thus, dental office personnel can visibly monitor the cotton rolls through the clear cylinder member, enabling easy viewing of the impurities captured by the cotton rolls, and determination of when replacement of the cotton rolls is necessary.

3 Claims, 1 Drawing Sheet

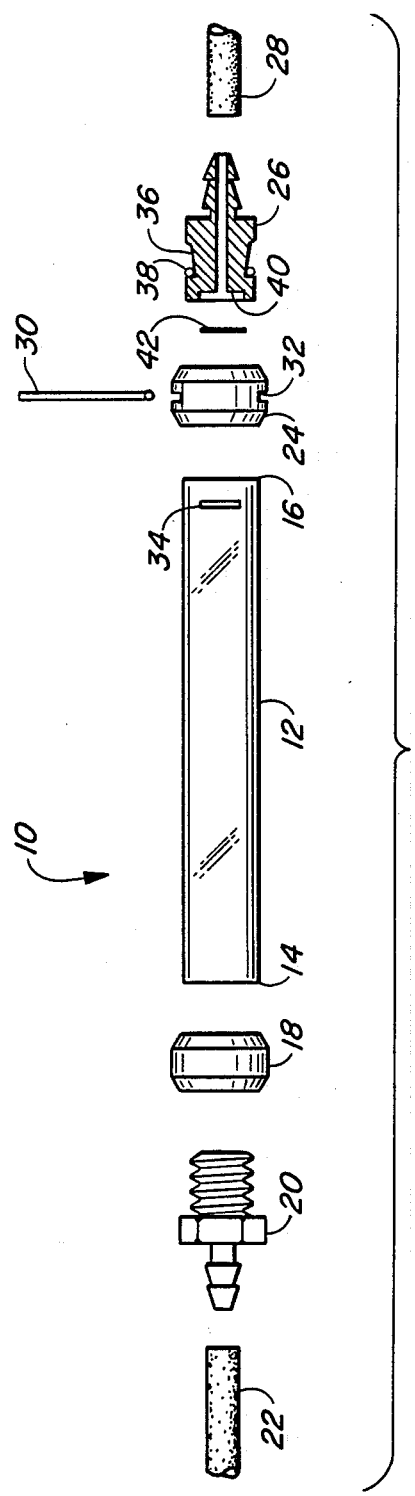
FIG._1.

FILTER DEVICE

This application is a continuation-in-part of copending application Ser. No. 185,896 filed Apr. 25, 1988, now abandoned.

BACKGROUND OF THE INVENTION

1. Field of the Invention

This invention relates generally to filters for air supply lines, and more specifically to an improved filter device for use with dental office syringe air supplies.

2. Description of the Prior Art

Dental office personnel have become increasingly aware of the need to upgrade dental office syringe air supply quality, primarily because of the changes in modern tooth restorative process techniques away from the use of amalgam and towards the use of composites, which yield a far more attractive restoration, but depend upon a chemical bond to adhere the composites to the tooth structure and provide good marginal seal and integrity. Thus, any impurities in the dental office air supply can adversely affect the bonding ability of the composites. Unfortunately, many dental offices have older air compressors which may be beginning to pump some oil vapors or other impurities, which vapors may migrate toward the point of use and affect bonding quality. Known commercial filter units for dental office air supply systems are typically unsightly and costly, thereby making them unsuitable for many dental office applications.

SUMMARY OF THE INVENTION

The filter device of this invention is designed for use in dental office syringe air supplies and relates to the necessity for extremely clean air in the preparation of a tooth to receive the new composite bonding materials being increasingly used in dental tooth restorations. The filter device comprises a clear plastic cylinder member with a pair of ends each bearing fittings conditioned to connect to the existing air supply line. Thus, the filter device can simply be connected to the end of the air supply line, or the line can be cut and the filter device spliced into the line at any appropriate point. At least one of the fittings bears a groove and retainer clip, or other quick-release feature, enabling ready access to that end of the cylinder member. The cylinder provides a housing for one or more standard cotton rolls, such as those typically used in a dental office, which provide the filtering medium. Thus, dental office personnel can visibly monitor the cotton rolls through the clear cylinder member, enabling easy viewing of the impurities captured by the cotton rolls, and determination of when replacement of the cotton rolls is necessary.

BRIEF DESCRIPTION OF THE DRAWINGS

FIG. 1 is an exploded side elevation view in partial cross section of the filter device of this invention, illustrating the insertion of the device into an air supply line, and the relative arrangement of the cylinder member and fittings.

DETAILED DESCRIPTION OF A PREFERRED EMBODIMENT

Referring now to FIG. 1 with greater particularity, filter device 10 of this invention comprises a clear plastic tube or cylinder 12 having an upstream end 14 and downstream end 16. Cylinder end 14 may be reinforced by upstream brass reinforcing ferrule 18, which in turn accepts upstream fitting 20 conditioned to engage air supply tubing end 22. In the preferred embodiment, ferrule 18 and fitting 20 are permanently secured to cylinder end 14. Cylinder end 16 may be reinforced by brass reinforcing ferrule 24, which releasably accepts downstream fitting 26, also conditioned to engage air supply tubing end 28. Downstream ferrule 24 is preferably permanently secured to cylinder end 16, while downstream fitting 26 is of a marginally narrower diameter and thus able to slide into and out of ferrule 24 and cylinder end 16.

Retaining clip 30 is captured by slot 32 in ferrule 24, and slot 34 in cylinder end 16, so that when fitting 26 is inserted into cylinder 12, insertion of retaining clip 30 prevents fitting 26 from sliding out, but removal of clip 30 permits quick disassembly and access to the cotton rolls inside cylinder 12 when necessary for their cleaning or replacement.

O-ring slot 36 on the circumferential surface of fitting 26 is slightly tapered with its diameter increasing in the downstream direction, so that O-ring 38 normally rests adjacent the upstream end (narrower diameter) of slot 36 when the filter is static (no air flow), enabling easy insertion and removal of the fitting 26. However, when the air supply is flowing and the filter device is pressurized, O-ring 38 is urged downstream and over the larger diameter portion of O-ring slot 36, thereby forming a seal against the inside diameter of cylinder 12.

Finally, downstream fitting 26 bears recess 40 to retain a screen 42, which prevents the cotton rolls or their captured detritus from entering tubing end 28.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims.

What is claimed as invention is:

1. A filter device for in-line insertion to syringe air supply tubing, said device comprising:
   a clear cylinder member having an inside surface, an upstream end and a downstream end;
   filter material contained in said cylinder member;
   an upstream fitting connected to said cylinder upstream end, said upstream fitting having means for releasable connection to said air supply tubing;
   a downstream fitting releasably connected to said cylinder downstream end, said downstream fitting having means for releasable connection to said air supply tubing, said downstream fitting having a circumferential surface bearing a tapered circumferential slot having an upstream side and a downstream side, wherein the depth of said slot decreases in the direction of said downstream side; and
   an O-ring carried by said downstream fitting tapered circumferential slot, wherein when said air supply is not flowing, said O-ring rests adjacent said slot upstream side, enabling said downstream fitting to be removed from said cylinder, and when said air supply is flowing, said O-ring is urged against said slot downstream side and seals against said cylinder inside surface.

2. The filter device of claim 1 wherein said filter material comprises cotton rolls.

3. The filter device of claim 1 including a retaining clip enabling releasable connection of said downstream fitting.

* * * * *